(12) United States Patent
Tegg et al.

(10) Patent No.: US 12,005,216 B2
(45) Date of Patent: Jun. 11, 2024

(54) ESOPHAGEAL DEVIATOR

(71) Applicant: St. Jude Medical, Cardiology Division, Inc., St. Paul, MN (US)

(72) Inventors: Troy Tegg, Elk River, MN (US); Salo Arias, Brooklyn Park, MN (US)

(73) Assignee: ST. JUDE MEDICAL, CARDIOLOGY DIVISION, INC., St. Paul, MN (US)

(*) Notice: Subject to any disclaimer, the term of this patent is extended or adjusted under 35 U.S.C. 154(b) by 270 days.

(21) Appl. No.: 17/127,336

(22) Filed: Dec. 18, 2020

(65) Prior Publication Data

US 2021/0275788 A1    Sep. 9, 2021

Related U.S. Application Data

(60) Provisional application No. 62/984,503, filed on Mar. 3, 2020.

(51) Int. Cl.
*A61M 29/00* (2006.01)
*A61M 25/00* (2006.01)
*A61M 25/01* (2006.01)

(52) U.S. Cl.
CPC ........ *A61M 29/00* (2013.01); *A61M 25/0108* (2013.01); *A61M 25/0136* (2013.01); *A61M 25/0147* (2013.01); *A61M 2025/0079* (2013.01); *A61M 2025/0166* (2013.01); *A61M 2205/3368* (2013.01); *A61M 2210/105* (2013.01)

(58) Field of Classification Search
CPC ............ A61B 18/1492; A61B 17/0218; A61B 2018/00577; A61B 2090/0427; A61B 2017/00243; A61B 2017/00238; A61M 25/0147; A61M 25/0136; A61M 25/0108; A61M 2205/3368; A61M 2210/105;
(Continued)

(56) References Cited

U.S. PATENT DOCUMENTS 5,170,803 A * 12/1992 Hewson ............... A61N 1/0517
607/124
5,558,665 A * 9/1996 Kieturakis ......... A61B 17/0218
606/1
(Continued)

OTHER PUBLICATIONS

"International Search Report and Written Opinion for PCT/US20/66062" dated Apr. 20, 2021.
(Continued)

*Primary Examiner* — Devin B Henson
(74) *Attorney, Agent, or Firm* — Billion & Armitage

(57) ABSTRACT

Embodiments include medical devices comprising a handle assembly including a wire tensioner component and an adjustment knob, the adjustment knob configured to rotate about a longitudinal axis of the handle assembly; an elongate shaft coupled to the handle assembly, the elongate shaft defining a lumen and including a deflectable section; a first wire coupled to the adjustment knob and extending from the adjustment knob through the lumen to at least a distal end portion of the deflectable section; and a second wire coupled to the wire tensioner component and extending from the wire tensioner component to at least the distal end portion of the deflectable section, the second wire having a deflectable extraluminal section configured to deflect independently of the deflectable section.

19 Claims, 10 Drawing Sheets

(58) Field of Classification Search
CPC .......... A61M 29/00; A61M 2025/0079; A61M 2025/0166
See application file for complete search history.

(56) References Cited

U.S. PATENT DOCUMENTS

| | | | | |
|---|---|---|---|---|
| 5,882,333 | A * | 3/1999 | Schaer | A61M 25/0144 604/95.01 |
| 7,197,354 | B2 | 3/2007 | Sobe | |
| 7,691,095 | B2 | 4/2010 | Bednarek et al. | |
| 8,147,486 | B2 | 4/2012 | Honour et al. | |
| 8,622,935 | B1 | 1/2014 | Leo | |
| 9,352,174 | B2 | 5/2016 | Sliwa | |
| 9,364,640 | B2 | 6/2016 | Vanney et al. | |
| 10,076,638 | B2 * | 9/2018 | Tran | A61M 25/0147 |
| 2003/0208219 | A1 * | 11/2003 | Aznoian | A61B 17/32056 604/95.04 |
| 2007/0225701 | A1 | 9/2007 | OSullivan | |
| 2011/0034936 | A1 | 2/2011 | Maloney | |
| 2013/0066193 | A1 | 3/2013 | Olson et al. | |
| 2017/0105715 | A1 | 4/2017 | Kasic | |
| 2017/0196479 | A1 | 7/2017 | Liu et al. | |
| 2018/0153436 | A1 | 6/2018 | Olson | |
| 2018/0317943 | A1 * | 11/2018 | Razavi | A61B 17/0218 |
| 2019/0134350 | A1 * | 5/2019 | Crisco | A61B 17/320016 |
| 2019/0223734 | A1 | 7/2019 | Akkireddy et al. | |
| 2019/0314109 | A1 | 10/2019 | Brucker et al. | |
| 2021/0015548 | A1 * | 1/2021 | Crawford | A61B 18/1492 |
| 2021/0186642 | A1 * | 6/2021 | Cohn | A61B 90/04 |

OTHER PUBLICATIONS

Cronin, et al., "The Year in Electrophysiology: Selected Highlights From 2018", Journal of Cardiothoracic and Vascular Anesthesia, Special Article, vol. 33, Issue 6, p. 1771-1777, Jun. 1, 2019, https://www.jcvaonline.com/article/S1053-0770(19)30085-0/fulltext.

Koruth, et al., "The Extent of Mechanical Esophageal Deviation to Avoid Esophageal Heating During Catheter Ablation of Atrial Fibrillation.", JACC Clin Electrophysiol 2017; 3:1146-1154.

Lakkireddy, et al., "Abstract 20927: Use of a Novel Pre-Shaped Nitinol Esophageal Deviator (EsoSure®) to Successfully Ablate the Left Atrium Without Esophageal Temperature Rise During Atrial Fibrillation Ablation: The Deflect Gut Study", Circulation, American Heart Association, originally published Jun. 9, 2018, 2017;136:A20927 https://www.ahajournals.org/doi/10.1161/circ.136.suppl_1.20927.

Pappone, et al., "Atrio-Esophageal Fistula After AF Ablation: Pathophysiology, Prevention & Treatment", Journal of Atrial Fibrillation, Oct.-Nov. 2013, vol. 6, Issue-3 https://www.ncbi.nlm.nih.gov/pmc/articles/PMC5153030/pdf/jafib-06-00860.pdf.

Parikh, et al., "easibility, Safety and Efficacy of a Novel Pre-Shaped Nitinol Esophageal Deviator to Successfully Deflect the Esophagus and Ablate Left Atrium without Esophageal Temperature Rise during Atrial Fibrillation Ablation—The Deflect Gut study,", Heart Rhythm (2018), doi: 10.1016/j.hrthm.2018.04.017. https://www.smarthealth-care.com/media/The-DEFLECT-GUT-Study-HRS.pdf.

* cited by examiner

ESOPHAGEAL DEVIATOR

FIELD OF THE INVENTION

The present invention generally relates to deflectable medical devices. More particularly, the present invention relates to medical devices for performing mechanical esophageal deviation.

BACKGROUND OF THE INVENTION

In the field of cardiac electrophysiology, catheter ablation is a minimally invasive procedure that can be utilized to manage cardiac arrhythmias, such as atrial fibrillation (AF). Such procedures typically involve advancing an ablating device through the vasculature of a patient to a site within the patient's heart. A practitioner can then selectively ablate target regions of tissue around the site to terminate abnormal electrical pathways and restore the heart's regular rhythm. Known ablating devices utilize radiofrequency ablation, microwave ablation, cryogenic ablation, and ultrasonic ablation. Use of these ablating devices poses a risk to patients, as the esophagus is particularly vulnerable to thermal injury due to the relative proximity of the line of ablation to the esophagus. For example, in some instances, ablating energy can have sufficient strength and intensity to pass through the target regions to non-target regions of tissue. In other instances, thermal damage can result simply due to the proximity of the esophagus to the target site within the heart.

Complications resulting from catheter ablation can include periesophageal injury and esophageal ulcerations. These complications, in the worst case, can lead to atrioesophageal fistula (AEF) formation. AEF is associated with high mortality and thus its prevention has been the subject of significant research. Methods of preventing AEF and other esophageal injuries include luminal esophageal temperature (LET) monitoring and mechanical esophageal displacement. LET monitoring employs temperature probes inserted through the mouth and into the esophagus of a subject. The temperature probes are relied upon as surrogate markers by the practitioner to determine whether and when to stop ablating to prevent injury to the esophagus. The challenge of LET monitoring is that the temperature probes suffer from various drawbacks, such as delayed or inaccurate temperature readings and an inability to determine the orientation and/or position of the temperature probe within the esophagus during procedures. Mechanical esophageal deviation is another technique utilized during ablation procedures. A challenge of mechanical esophageal deviation devices is that current esophageal deviators all require the use of contrast to visualize and confirm esophageal displacement.

SUMMARY OF THE INVENTION

In general, the present invention relates to medical systems, medical devices, and components of each that may be utilized to perform, visualize, and/or confirm displacement of the esophagus away from an ablation site in real time without the use of contrast.

In one embodiment, a medical system comprising a medical device and a medical imaging and/or positioning system is provided. The medical device may include a handle assembly including a wire tensioner component and an adjustment knob, the adjustment knob configured to rotate about a longitudinal axis of the handle assembly; an elongate shaft coupled to the handle assembly, the elongate shaft defining a lumen and including a deflectable section; a first wire coupled to the adjustment knob and extending from the adjustment knob through the lumen to at least a distal end portion of the deflectable section; a second wire coupled to the wire tensioner component and extending from the wire tensioner component to at least the distal end portion of the deflectable section, the second wire having a deflectable extraluminal section configured to deflect independently of the deflectable section; and optionally one or more sensors mounted on or near the deflectable section of the elongate shaft and/or the deflectable extraluminal section of the second wire. The medical imaging and/or positioning system may include an electrical impedance-based system, an optical sensing-based system, and/or an ionizing radiation-based system.

In another embodiment, a medical device for displacing an esophagus of a subject during a medical procedure is provided. The medical device may include a handle assembly including a wire tensioner component and an adjustment knob, the adjustment knob configured to rotate about a longitudinal axis of the handle assembly; an elongate shaft coupled to the handle assembly, the elongate shaft defining a lumen and including a deflectable section; a first wire coupled to the adjustment knob and extending from the adjustment knob through the lumen to at least a distal end portion of the deflectable section; a second wire coupled to the wire tensioner component and extending from the wire tensioner component to at least the distal end portion of the deflectable section, the second wire having a deflectable extraluminal section configured to deflect independently of the deflectable section; and optionally one or more sensors mounted on or near the deflectable section of the elongate shaft and/or the deflectable extraluminal section of the second wire.

In a further embodiment, a deflectable member of a medical device for displacing an esophagus of a subject during a medical procedure is provided. The deflectable member may include an elongate shaft, the elongate shaft defining a lumen and including a deflectable section, wherein the deflectable section is configured to shift between a neutral position and a deflected position through activation of a first wire; a second wire having a deflectable extraluminal section extending between proximal and distal end portions of the deflectable section, wherein the deflectable extraluminal section is configured to deflect independently of the deflectable section; and optionally one or more sensors mounted on or near the deflectable section of the elongate shaft and/or the deflectable extraluminal section of the second wire.

The details of one or more examples are set forth in the description below. Other features, objects, and advantages will be apparent from the description and from the claims.

DETAILED DESCRIPTION

Figure 1:
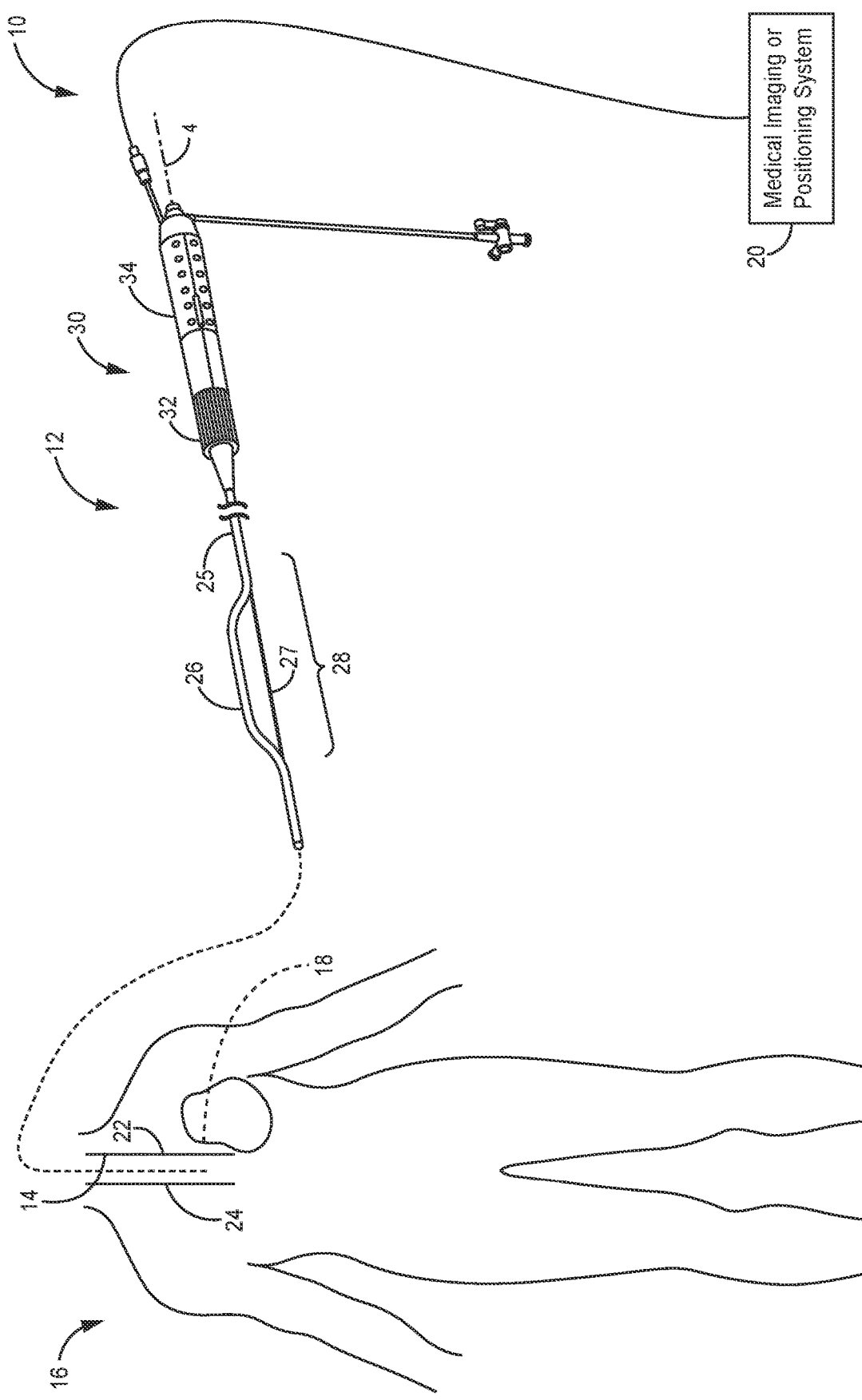
FIG. 1 is a diagrammatic view of a representative system including a medical device for displacing the esophagus of a subject, in accordance with an embodiment of the invention.

FIG. 1 is a diagrammatic view of a representative medical system 10 for use in ablation procedures, among other medical procedures. As shown in FIG. 1, in one embodiment, the medical system 10 may include a medical device 12 and a medical imaging and/or positioning system 20. The medical device 12 may be used for displacing the esophagus 14 of a subject 16 away from, for example, an ablation site 18 and may include an elongate shaft 25 and a wire 27, each coupled to a handle assembly 30 or a portion thereof and each including deflectable sections 26 and 28. The deflectable section 26 may be configured to deflect against and thus displace a first esophageal edge in response to user manipulation of the handle assembly 30. The deflectable section 28 may be configured to deflect independently of deflectable section 26 and in response to contact with a second esophageal edge. One or more sensors may optionally be mounted on or run through one or both of the deflectable sections 26 and 28. The one or more sensors may include, for example, one or more of electrodes, multi-core fibers, and radiopaque marker bands. The sensors, when used in combination with medical imaging and/or positioning system 20 for detection purposes (e.g., at least one of an electrical impedance-based system, optical sensing-based system, ionizing radiation-based system, and the like), permit visual confirmation of esophageal displacement without the use of contrast agents.

In a typical procedure and in accordance with another embodiment, a user may insert at least a portion of the deflectable sections 26 and 28 into the esophagus 14 of a subject 16 through the mouth. Once oriented in the esophagus 14, the user may manipulate the handle assembly 30 (e.g., by rotating an adjustment knob 32 rotateably coupled to a handle grip 34 about a longitudinal axis 4 of the handle assembly 30), to cause the deflectable section 26 of the elongate shaft 25 to deflect against and displace a leading esophageal edge 24. Displacement of the leading esophageal edge 24 should cause the trailing esophageal edge 22 to be displaced with it. Such displacement should also bring the trailing esophageal edge 22 in contact with wire 27 which causes the deflectable section 28 to deflect in response thereto. The user may then refer to the medical imagining and/or positioning system 20 to determine the configuration of the deflectable section 28. If observed in a deflected position, a user may conclude that the trailing esophageal edge 22 has been displaced and proceed with the ablation procedure. If observed in a neutral (e.g., undeflected) position, a user may conclude that the esophagus 14 is undergoing esophageal stretching (e.g., where leading esophageal edge, but not the trailing esophageal edge, is displaced) and decide not to proceed any further with the ablation procedure.

The ablation procedures in which the medical systems and devices described herein may be used are generally not particularly limited. In some embodiments, the medical systems and devices may be employed in catheter ablation procedures to prevent thermal injury to esophageal tissue due to the relative proximity of the esophagus to the ablation site. For example, the medical device may be employed in cardiac ablation procedures for treating cardiac arrhythmias, such as atrial fibrillation and ventricular tachycardia, among others. Accordingly, embodiments include use of the medical device in endocardial or epicardial ablation procedures of the pulmonary vein and posterior wall, among other ablations of the left atrium. The medical device may also be employed in bronchial ablation procedures for treating conditions of the pulmonary system, such as asthma, among others. These shall not be limiting. Other ablation procedures may be employed without departing from the scope of the present disclosure.

Figure 2:
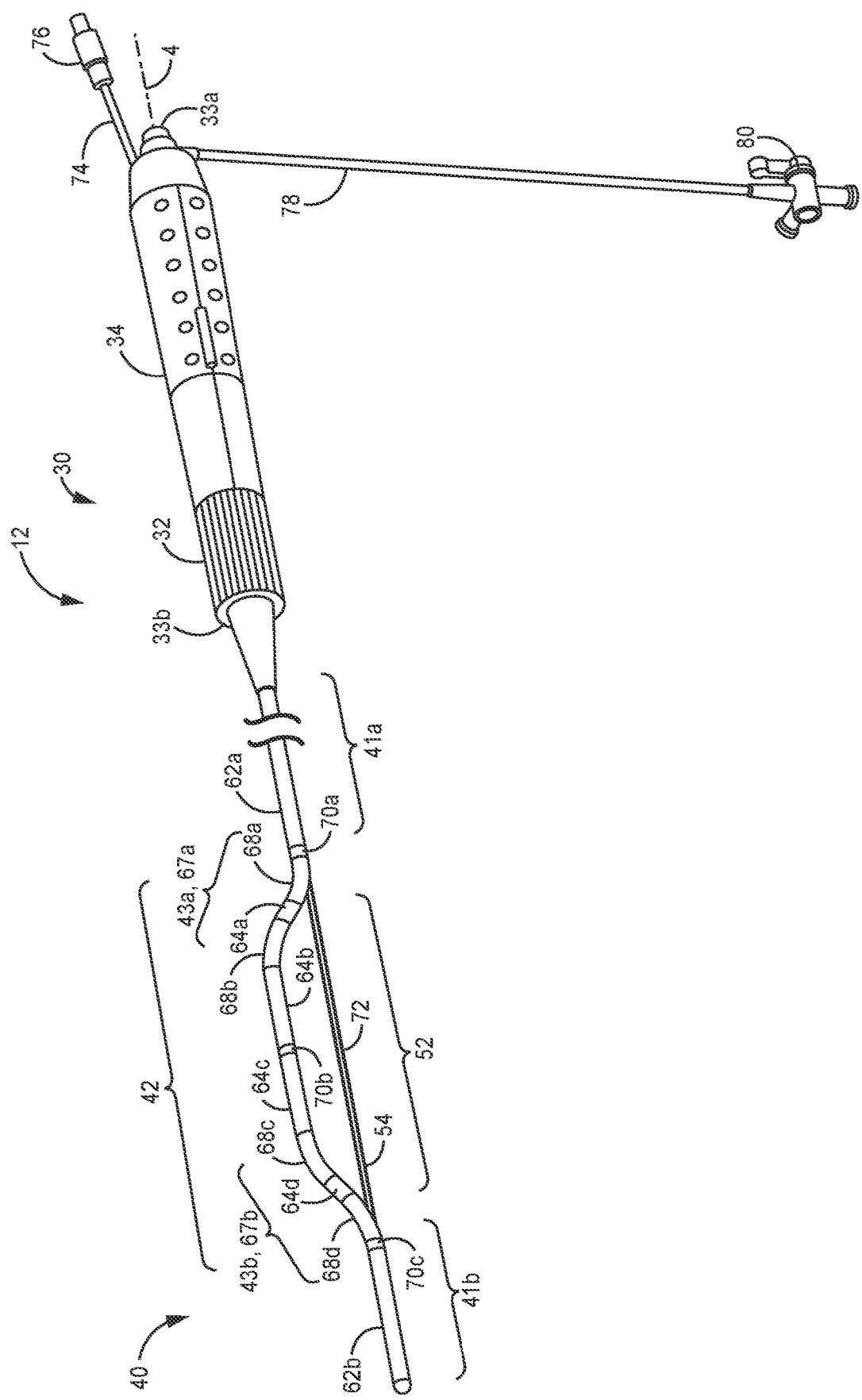
FIG. 2 is an isometric view of a medical device where the medical device includes an esophageal deviator, in accordance with an embodiment of the invention.

Referring now to FIG. 2, in one embodiment, the medical device 12 includes an esophageal deviator which is shown in a neutral position. The esophageal deviator 12 may generally include a handle assembly 30, an elongate shaft 40, a deflectable section 42, a first wire 44 (not shown), a second wire 54, a deflectable extraluminal section 52, and optionally one or more sensors 70a, 70b, 70c, and 72. The handle assembly 30 may be coupled to the elongate shaft 40. The elongate shaft 40 may define a lumen and include the deflectable section 42. The deflectable section 42 may include proximal 43a and distal 43b end portions and may be configured to deflect in response to user manipulation of the handle assembly 30. Proximal ends of the first wire 44 (not shown) and second wire 54 may be at least partially disposed in the lumen and internally linked to the handle assembly 30, for example, via adjustment knob 32 and a wire tensioner component (not shown), respectively. The first 44 and second 54 wires may generally extend from the handle assembly 30 to at least about the distal end portion 43b of the deflectable section 42. The first wire 44 may be or include an on- or off-axis intraluminal wire disposed entirely within the lumen. The second wire 54 may be or include an on- or off-axis wire having one or more intraluminal sections and at least one extraluminal section, such as deflectable extraluminal section 52. The deflectable extraluminal section 52 may extend extraluminally from about the proximal end portion 43a to about the distal end portion 43b. The deflectable extraluminal section 52 may be configured to deflect independently of the deflectable section 42.

The handle assembly 30 may define a lumen and include a wire tensioner component (not shown), an adjustment knob 32, and a handle grip 34. The adjustment knob 32 may be rotateably coupled to the handle grip 34 and configured to rotate in a first direction (e.g., a clockwise or counter-clockwise direction) about a longitudinal axis 4 of the handle assembly 30. A proximal end 33a of the handle assembly 30 may be connected to tubing 74 and 78. Tubing 74 may extend to connector 76, and tubing 78 may extend to connector 80. The connectors 76 and 80 may provide one or more of mechanical, fluid, optical, and electrical connections for tubing 74 and 78. For example, in one embodiment, the tubing 74 may contain electrical wires and extend to an electrical connector 76 for connecting to medical imaging or positioning systems 20. In another embodiment, the tubing 74 may transmit light and extend to an optical connector 76 for connecting to optical sensing-based systems. In another embodiment, the tubing 78 may extend to stopcock 80 and may be adapted to deliver fluid (e.g., chilled water or other cooling irrigant) from a fluid source through at least a portion of the lumen defined by the handle assembly 30 and/or elongate shaft 40. The tubing 74 and 78 and connector 76 and 80 may comprise other conventional components known in the art.

A distal end 33b of the handle assembly may be coupled to the elongate shaft 40. The elongate shaft may include a first section 41a, a second section 41b, and the deflectable section 42. The first section 41a and second section 41b may be provided on opposing sides of the deflectable section 42. For example, the first section 41a may be proximal to the deflectable section 42 and the second section 41b may be distal to the deflectable section 42. In one embodiment, the first section 41a and second section 41b of the elongate shaft 40 may include rigid sections 62a and 62b, respectively. Rigid section 62a may be disposed between the handle assembly 30 and the proximal end portion 43a of the deflectable section 42. Rigid section 62b may be disposed between the distal end portion 43b of the deflectable section 42 and the extreme distal end of the elongate shaft 40. In another embodiment, the first section 41a and second section 41b of the elongate shaft 40 may include or further include one or more additional rigid sections and/or one or more compressible sections, or may exclude one or more of the rigid sections 62a and 62b. For example, one or more compressible sections may be disposed between or adjacent to rigid sections 62a and 62b, or may replace at least one of the rigid sections 62a and 62b.

The deflectable section 42 may include a combination of rigid sections and compressible sections. For example, as shown in FIG. 2, the deflectable section 42 may include rigid sections 64a, 64b, 64c, and 64d and compressible sections 68a, 68b, 68c, and 68d. More specifically, in the illustrated embodiment, the deflectable section 42 may include rigid sections 64b and 64c disposed between proximal compressible joint 67a and distal compressible joint 67b. The proximal compressible joint 67a may be provided at or near the proximal end portion 43a of the deflectable section 42. The proximal compressible joint 67a may include rigid section 64a disposed between compressible sections 68a and 68b. The distal compressible joint 67b may be provided at or near the distal end portion 43b of the deflectable section 42. The distal compressible joint 67b may include rigid section 64d disposed between compressible sections 68c and 68d. While the proximal 67a and distal 67b compressible joints are shown including rigid sections between two compressible sections, in another embodiment, the proximal 67a and distal 67b compressible joints may each independently include one or more additional rigid sections, one or more additional compressible sections, only a single compressible section, and/or one or more compressible sections. In addition, in another embodiment, the rigid sections disposed between the proximal 67a and distal 67b compressible joints may include a single continuous rigid section and/or one or more additional rigid sections.

In one embodiment, the proximal 67a and distal 67b compressible joints may be formed with a slight curve such that the deflectable section 42 also has a slight curvature while in a neutral position. Although not required, the curve in the proximal 67a and distal 67b compressible joints may facilitate deflection of the deflectable member 42. In another embodiment, the deflectable section 42 includes proximal 67a and distal 67b compressible joints which are not curved or which are curved to a lesser extent.

As described above and in more detail below, the first 44 and second 54 wires generally extend from the handle assembly 30 through at least a portion of the lumen of the elongate shaft 40 to at least about a distal end portion 43b of the deflectable section 42. The first wire 44 may include an intraluminal wire of any shape disposed entirely in the lumen of the elongate body 40. For example, in one embodiment, the intraluminal wire is a flat wire with a rectangular- or square-shaped cross-section. In another embodiment, the intraluminal wire is a rounded wire. Other shapes are possible and within the scope of the present invention. The second wire 54 may include one or more intraluminal and extraluminal sections. The extraluminal section may include, for example, the deflectable extraluminal section 52. The second wire 54 may have any of the shapes of the first wire 44. The materials used to form the first 44 and second 54 wires are not particularly limited. For example, the first 44 and second 54 wires may be formed from a superelastic nickel-titanium (known as NiTi or Nitinol) wire, carbon fiber, para-aramid synthetic fiber generally available from DuPont under the brand name KEVLAR®, or other suitable material in accordance with the embodiments of the present disclosure.

Each of the first and second wire may be independently adapted to carry a tensile load, a compressive load, a tensile and compressive load, or neither a tensile nor a compressive load. In some embodiments, for example, the deflectable section 42 may be deflected by placing the first wire 44 in tension and may be returned to a neutral position by releasing the tension on the first wire 44 (e.g., without placing the first wire 44 in compression) or by placing the first wire 44 in compression. In some embodiments, deflectable extraluminal section 52 may be deflected in response to contact with the esophagus (e.g., a trailing esophageal edge), optionally without applying any tensile or compressive force to the second wire 54. In some embodiments, the second wire 54 is coupled to a wire tensioner component, such as a spring, which is disposed in the handle assembly 30 and permits the deflectable extraluminal section 52 to deflect independently of the deflectable section 42. For example, in some embodiments, the wire tensioner component is configured to elongate in response to the esophageal edge making contact with the second wire 54, thereby allowing the deflectable extraluminal section 52 to deflect. In some embodiments, when the deflectable section 42 is in a neutral or undeflected position, the wire tensioner component is placed under tension (e.g., elongates); and when the deflectable section 42 is in a deflected position, the second wire 54 is placed under compression, at least until the second wire 54 is deflected (e.g., in response to contact with an esophageal edge) at which point the wire tensioner component may be placed under tension. In these embodiments, the second wire 54 may be fixably coupled, or bonded to at least one of the wire guide 84 (discussed below) and first wire 44, at the distal end portion 43b of the deflectable section 42. In some embodiments, the deflectable extraluminal section 52 may be returned to a neutral position by manually doing so (e.g., via user manipulation), by releasing any tensile and/or compressive load on the second wire 54, and/or by placing the second wire 54 in tension.

For example, in one embodiment, the first wire 44 may be coupled to the adjustment knob 32 and the second wire 54 may be coupled to a wire tensioner component, such as a spring, disposed in the handle assembly 30. In this embodiment, rotating the adjustment knob 32 in a first direction (e.g., a clockwise or counterclockwise direction) may compress the proximal 67a and distal 67b compressible joints of the deflectable section 42, causing the rigid sections 64b and 64c to bow outwardly and the deflectable section 42 to deflect. Being attached to the wire tensioner component, the second wire 54 may exist in a neutral or undeflected position at least until an esophageal edge (e.g., a trailing esophageal edge) makes contact with the second wire 54, wherein said contact causes the second wire 54 and thus the deflectable extraluminal section 52 to deflect. Once the deflectable section 42 has been deflected, the adjustment knob 32 may be rotated in the other direction to return the deflectable section 42 to a neutral or undeflected position.

One or more sensors may optionally be mounted on or run through any portion of the elongate shaft 40, the deflectable section 42, and/or the deflectable extraluminal section 52. As shown in FIG. 2, in one embodiment, electrode rings 70a, 70b, and 70c may be mounted on the elongate shaft 40, and electrode ring 72 may be mounted on the deflectable extraluminal section 52. More specifically, electrode ring 70a may be mounted near the proximal end portion 43a of the deflectable section 42 adjacent to compressible section 68a. Electrode ring 70c may be mounted near the distal end portion 43b of the deflectable section 42 adjacent to compressible section 68d. Electrode ring 70b may be mounted between the rigid sections 64b and 64c, and electrode ring 72 may be mounted on the deflectable extraluminal section 52. While not required, by centering the electrode rings 70b and 72 as shown in FIG. 2, the electrode rings 70b and 72 may be positioned at or near the apex of the deflectable section 42 and deflectable extraluminal section 52 when each of those sections 42, 52 are configured in a deflected position. While the positioning and number of electrode rings has been described as shown in FIG. 2, a skilled person will readily appreciate other configurations including additional or fewer electrodes in the same or different positions.

Other sensors may be used herein to permit visual confirmation of displacement, either with or in place of the electrodes 70a, 70b, 70c, 72. Non-limiting examples of such other sensors include one or more of radiopaque marker bands and fiber optic shape sensing multi-core fibers, among others. For example, in one embodiment, one or more multi-core fibers are used, each multi-core fiber including one or more fiber cores and each fiber core including one or more fiber Bragg gratings (FBGs). The multi-core fibers may extend from and to any portion within the lumens of the handle assembly 30 and/or the elongate shaft 40. In another embodiment, one or more radiopaque marker bands are used. The radiopaque marker bands may be made of materials such as one or more of barium sulfate, gold, platinum, tungsten, tantalum, iridium, and alloys comprising at least two of those materials. The radiopaque marker bands may be mounted on any portion of the elongate shaft 40 and/or second wire 54. In addition to these sensors, one or more temperature sensors for sensing temperature of or within the esophagus may also be mounted on any portion of the elongate shaft 40, second wire 54, and/or run through the lumen of the elongate shaft 40. Non-limiting examples of temperature sensors include one or more of thermocouples, thermistors, fiber cores, a core of a multi-core fiber, and the like.

Figure 3A:
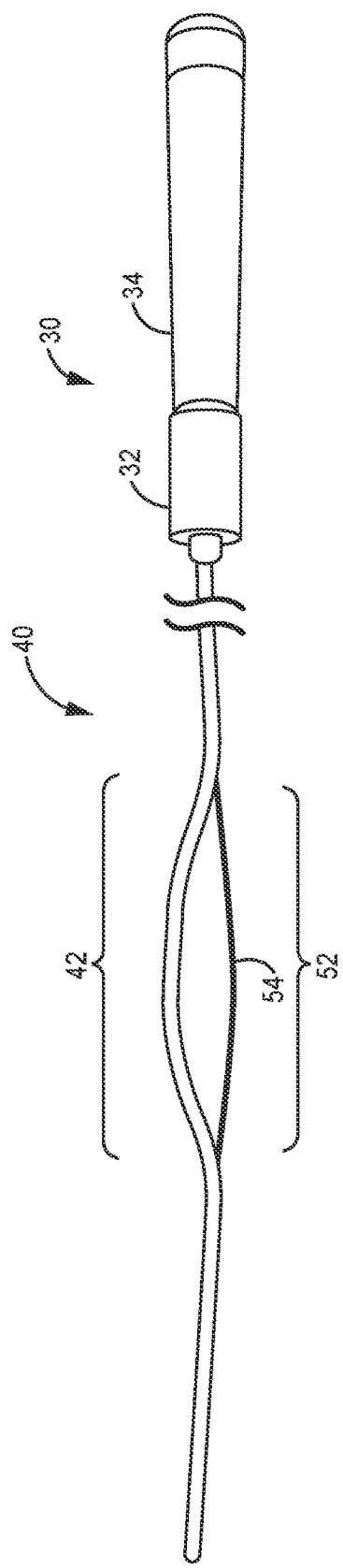
FIG. 3A is a plan view of the esophageal deviator with a deflectable section of the elongate shaft and a deflectable extraluminal section of a wire shown in neutral or undeflected positions, in accordance with an embodiment of the invention.
Figure 3B:
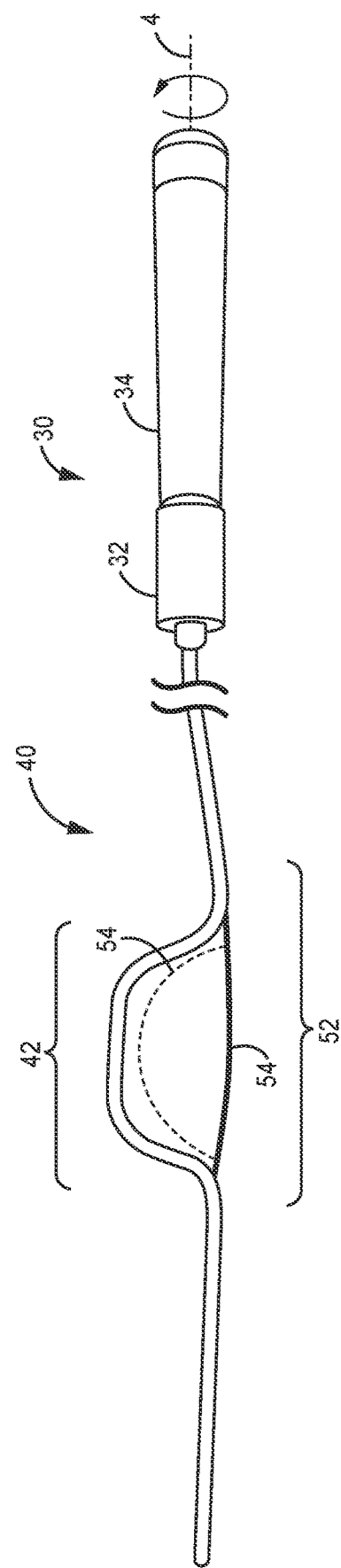
FIG. 3B is a plan view of the esophageal deviator with the deflectable section shown in a deflected position and the deflectable extraluminal section shown in neutral and deflected positions, in accordance with an embodiment of the invention.

Referring now to FIGS. 3A and 3B, plan views of the esophageal deviator with a deflectable section of the elongate shaft and a deflectable extraluminal section of a wire shown in neutral or undeflected positions (FIG. 3A), and with the deflectable section shown in a deflected position and the deflectable extraluminal section shown in neutral and deflected positions (FIG. 3B) are shown, in accordance with an embodiment of the invention. In some embodiments, the deflectable section 42 and deflectable extraluminal section 52 each may be independently configurable between neutral and deflected positions. In one embodiment, the neutral position may be useful for inserting and/or removing the esophageal deviator 12 from a subject's esophagus. In another embodiment, the deflected position may be useful for displacing the esophagus and/or confirming esophageal displacement (e.g., or esophageal stretching). As illustrated in FIG. 3A, in some embodiments, the deflectable section 42 and deflectable extraluminal section 52 may have a slight curvature while in neutral (e.g., undeflected) positions. While in such a neutral position, the first wire 44 and/or second wire 54 may not be placed in tension or compression or any tensile or compressive forces upon the first 44 and/or second 54 wires may be minimal. In other embodiments, the deflectable section 42 and/or deflectable extraluminal section 52 may have no curvature or may be curved to a lesser extent while in a neutral position.

As illustrated in FIG. 3B, in some embodiments, the deflectable section 42 may be in a deflected position, while the deflectable extraluminal section 52 may be in a neutral position. In this way, the deflectable section 42 and deflectable extraluminal section 52 may be configured to deflect independently of each other. For example, in one embodiment, the deflectable section 42 may be in a deflected position in response to user manipulation of the handle assembly 30, while the deflectable extraluminal section 52 may be in a neutral position prior to making contact with the trailing esophageal edge or while the esophagus is merely being stretched. In other embodiments, the deflectable section 42 and deflectable extraluminal section 52 may both be in deflected positions. For example, in one embodiment, the deflectable section 42 and deflectable extraluminal section 52 (which depicted using dashed lines in FIG. 3B) may be in deflected positions following user manipulation of the handle assembly 30 and following contact with the trailing esophageal edge, respectively, which may indicate that the leading and trailing esophageal edges have been displaced or laterally displaced, for example, away from the line of ablation.

Figure 4:
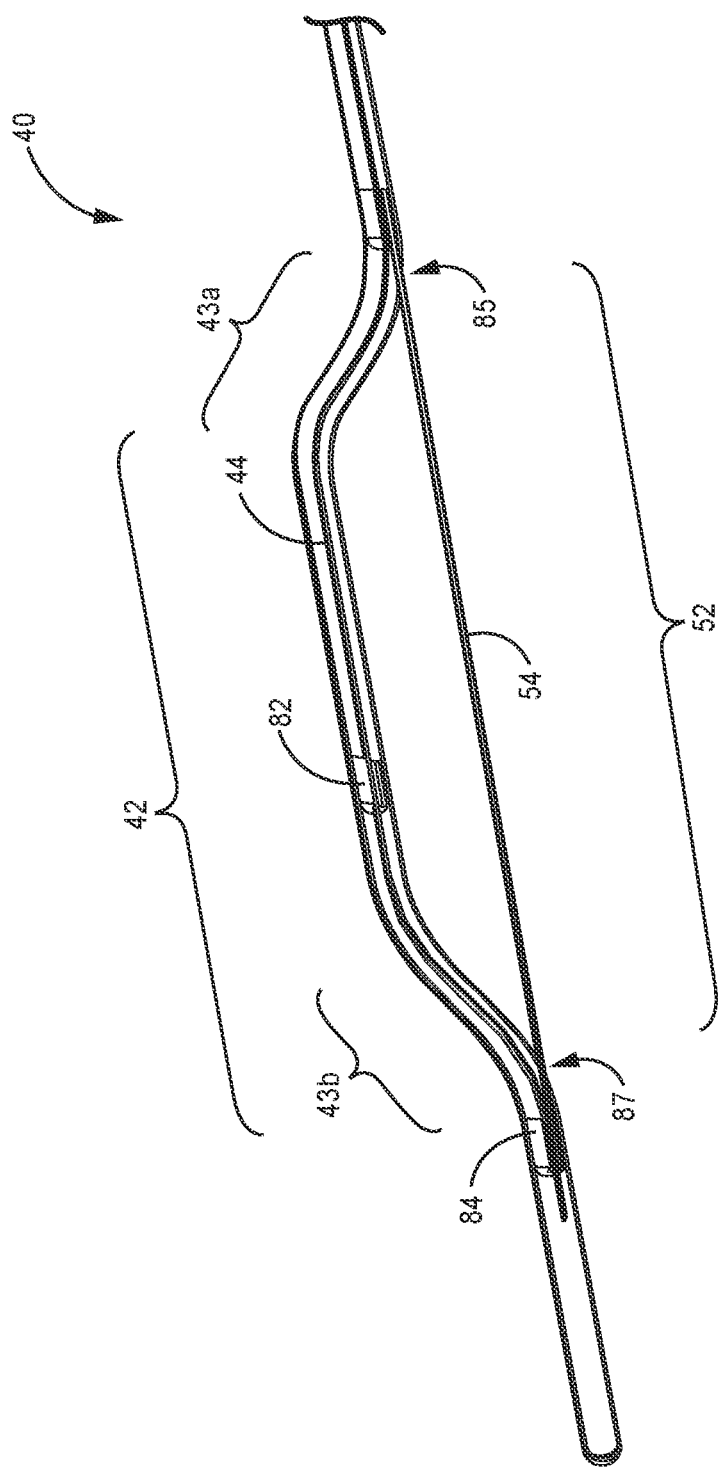
FIG. 4 is a cutaway view of a portion of the elongate shaft, in accordance with an embodiment of the invention.
Figure 5A:
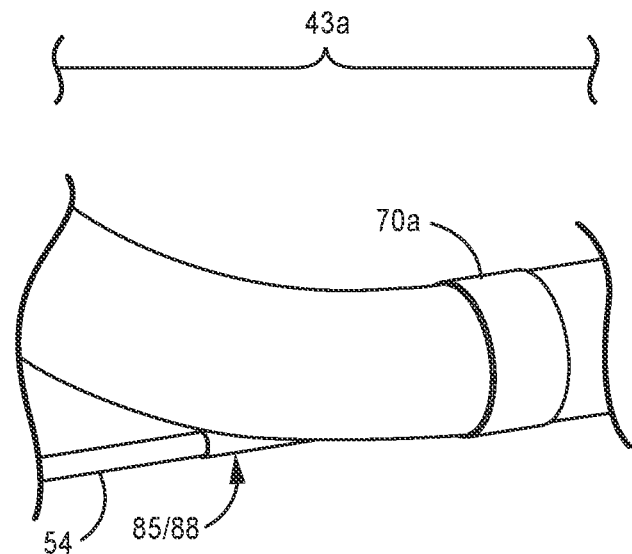
FIGS. 5A and 5B are isometric views of the proximal and distal end portions of the deflectable section with ports for the deflectable extraluminal section, in accordance with an embodiment of the invention.
Figure 5B:
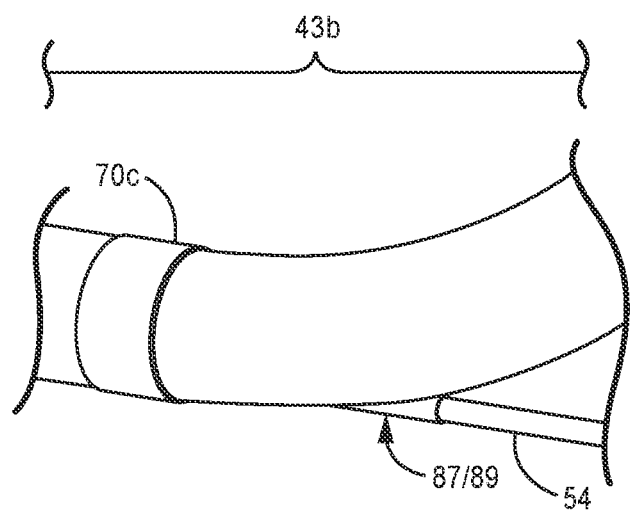

Referring now to FIGS. 4 and 5A-5B, a cutaway view of a portion of the elongate shaft (FIG. 4) and isometric views of the proximal and distal end portions of the deflectable section with ports for the deflectable extraluminal section (FIGS. 5A-5B) are shown, in accordance with embodiments of the invention. In one embodiment, the first wire 44 may be an intraluminal wire that generally extends within the lumen of the elongate shaft 40, either along at least a portion of the shaft or along the entirety of the shaft. For example, in one embodiment, the first wire 44 is an intraluminal wire that extends from the handle assembly 30 (not shown) and, in particular, from the adjustment knob 32 (not shown) through wire guides 82 and 84 to at least about the distal end portion 43b of the deflectable section 42. Similarly, the second wire 54 may generally extend from the handle assembly 30 (not shown) and, in particular, from the wire tensioner component (not shown) to at least about the distal end portion 43b of the deflectable section 42. However, unlike the first wire 44, the second wire 54 may include an extraluminal section in addition to intraluminal sections. For example, in one embodiment, the intraluminal section of the second wire 54 may extend from the wire tensioner component (not shown) through the lumen of the elongate shaft 40 to about the proximal end portion 43a of the deflectable section 42. At or near the proximal end portion 43a, the second wire 54 may exit the lumen through port 85 and extend extraluminally to about the distal end portion 43b of the deflectable section 42. At or near the distal end portion 43b, the second wire 54 may reenter the lumen through port 87 and may extend intraluminally for a distance to wire guide 84 where the first 44 and second 54 wires may be brought into physical contact and optionally bonded.

As illustrated in FIGS. 5A and 5B, in one embodiment, the first port 85 may be provided at or near the proximal end portion 43a of the deflectable section 42 and the second port 87 may be provided at or near the distal end portion 43b of the deflectable section 42. The first 85 and second 87 ports may include openings (e.g., passages, slits, etc.) and/or structural members through which the second wire 54 may exit and enter the lumen of the elongate shaft 40, respectively. For example, in one embodiment, the first port 85 and second port 87 may include cylindrical members 88 and 89, respectively, coupled to and protruding from the elongate shaft 40. The cylindrical members 88 and 89 may optionally have an inner circumferential shape adapted to fit the outer circumferential shape of the second wire 54. In another embodiment, the first port 85 and second port 87 may include passages or slits formed in the wall of the elongate shaft 40. Similarly, the passages or slits may optionally have an inner circumferential shape adapted to fit the outer circumferential shape of the second wire 54. The openings and/or structural members may optionally form a seal around the second wire 54, which may be desirable to prevent the exchange of fluid from the lumen to the subject's esophagus and from the esophagus to the lumen. Conventional components known in the art (e.g., retaining or mounting rings, sealants, adhesives, and the like) may also be included to secure and/or seal the second wire.

In addition or in the alternative, in some embodiments, the first 85 and/or second 87 ports may be adapted to permit the second wire 54 to slide or move through at least one or both of the first 85 and second ports 87. For example, in one embodiment, the first port 85 may be slidably coupled with the second wire 54 so as to permit the second wire 54 to move through the first port 85 while the deflectable section 42 is moved from a neutral position to a deflected position. In this embodiment, the second port 87 may similarly be adapted to permit movement over the second wire 54, or it may be adapted to permit no movement (e.g., fixably coupled to the second wire 54). Other configurations are possible. For example, in other embodiments, the first port 85 may be slidably coupled to the second wire 54 or fixably coupled to the second wire 54, and the second port 87 may be slidably coupled to the second wire 54 or fixably coupled to the second wire 54. Any combination of the preceding configurations may be utilized herein without departing from the scope of the present invention.

Figure 6:
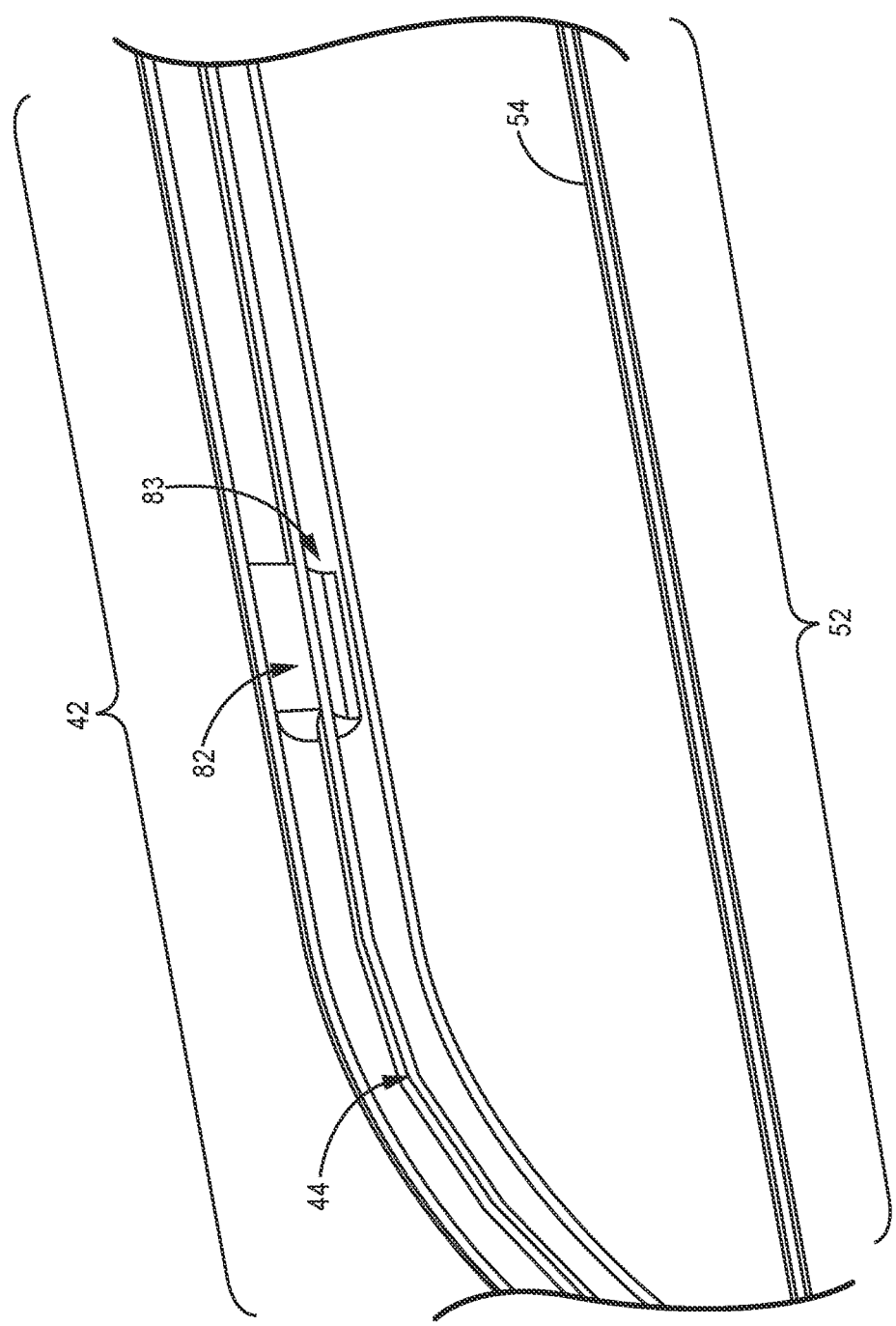
FIG. 6 is a cutaway view of a portion of the deflectable section, in accordance with an embodiment of the invention.
Figure 7:
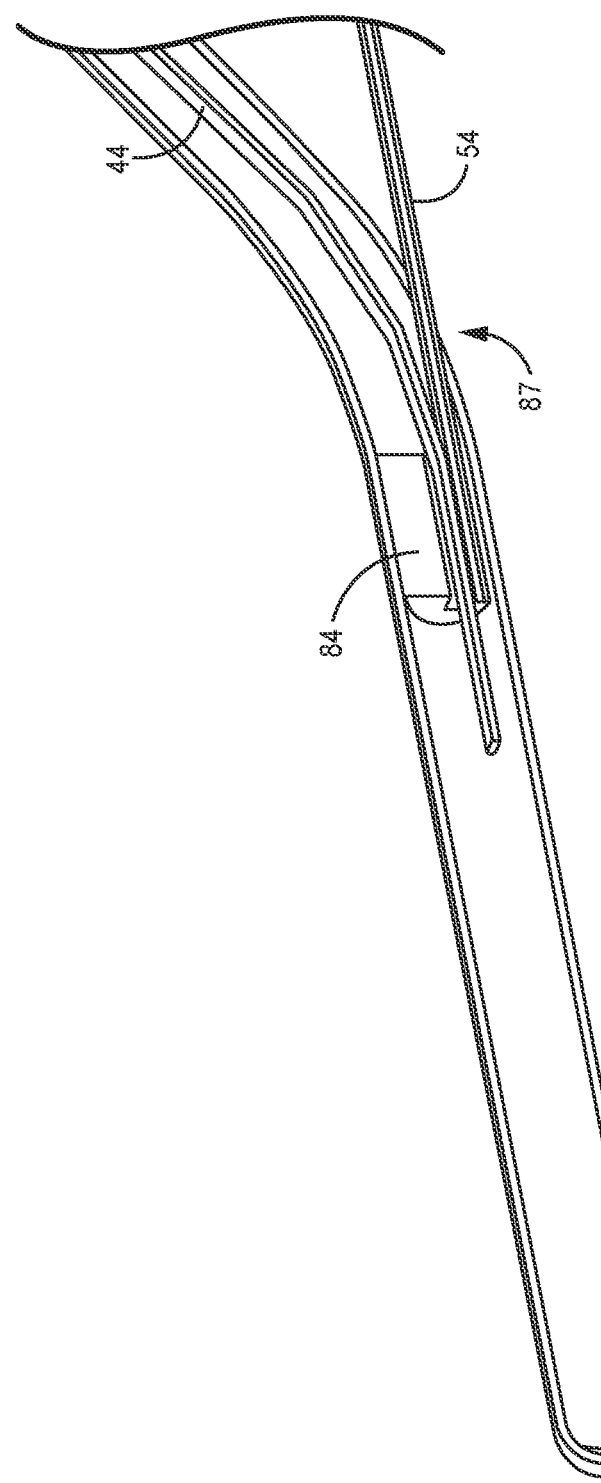
FIG. 7 is a cutaway view of the distal end portion of the deflectable section, in accordance with an embodiment of the invention.

Referring now to FIGS. 6 and 7, a cutaway view of a portion of the deflectable section (FIG. 6) and a cutaway view of the distal end portion of the deflectable section (FIG. 7) are shown, in accordance with embodiments of the invention. As shown in FIG. 6, wire guide 82 may be disposed in or near the rigid sections of the deflectable section, such as rigid sections 64b and 64c of the deflectable section 42. Wire guide 82 may include passages for the first wire 44 and passage 83 for other wires, such as conducting wires electrically connected to ring electrodes 70b and/or 70c. In another embodiment, the wire guide 82 may include or further include other passages for multi-core fibers, temperature sensors and its wires, and the like. In one embodiment, the passages are formed in the wire guide 82 such that the orientation of the first wire 44 and/or any of the other wires is on-axis (e.g., oriented on or along a central longitudinal axis). In another embodiment, the passages are formed in the wire guide 82 such that the orientation of the first wire 44 and/or any of the other wires is off-axis (e.g., not oriented on or along a central longitudinal axis). As illustrated in FIG. 7, wire guide 84 may be disposed in or near the distal end portion 43b of the deflectable member 42. Wire guide 84 may include passages for the first wire 44 and/or second wire 54, which may enter through second port 87. In embodiments, the first 44 and second wires 54 may be in physical contact via wire guide 84, slidably coupled to wire guide 84, or bonded to each other and/or to wire guide 84. Alternatively, at least one of the first 44 and second wire 54 may be bonded to wire guide 84. Any combination of these coupling techniques may also be utilized. Wire guide 84 may similarly include or further include passages for wires for electrodes, multi-core fibers, temperature sensors, and the like. In addition, the passages may be formed in the wire guide 84 such that the wires are oriented on-axis or off-axis.

Wire guides 82 and 84 may be attached or bonded to the inner surface of the elongate shaft 40. The mechanisms of attachment of wire guides 82 and 84 to the lumen are not particularly limited. For example, wire guides 82 and 84 may be adhesively bonded, thermally bonded, or radiofrequency bonded to the lumen, among other mechanisms of attachment. In addition, while FIGS. 6 and 7 show the wire guides 82 and 84 in specific locations in the lumen of the elongate shaft 40, in general, the positioning and number of wire guides are not particularly limited. For example, additional wire guides may be included in the elongate shaft 40, or fewer wire guides may be used, and the wire guides may be located elsewhere throughout the elongate shaft 40. In one embodiment, one or more additional wire guides may be disposed in the first section 41a of the elongate shaft, proximal end portion 43a of the deflectable section 42, deflectable section 42, and/or distal end portion 43b of the deflectable section 42. In another embodiment, the elongate shaft 40 may not include any wire guides or may include only one wire guide.

Figure 8:
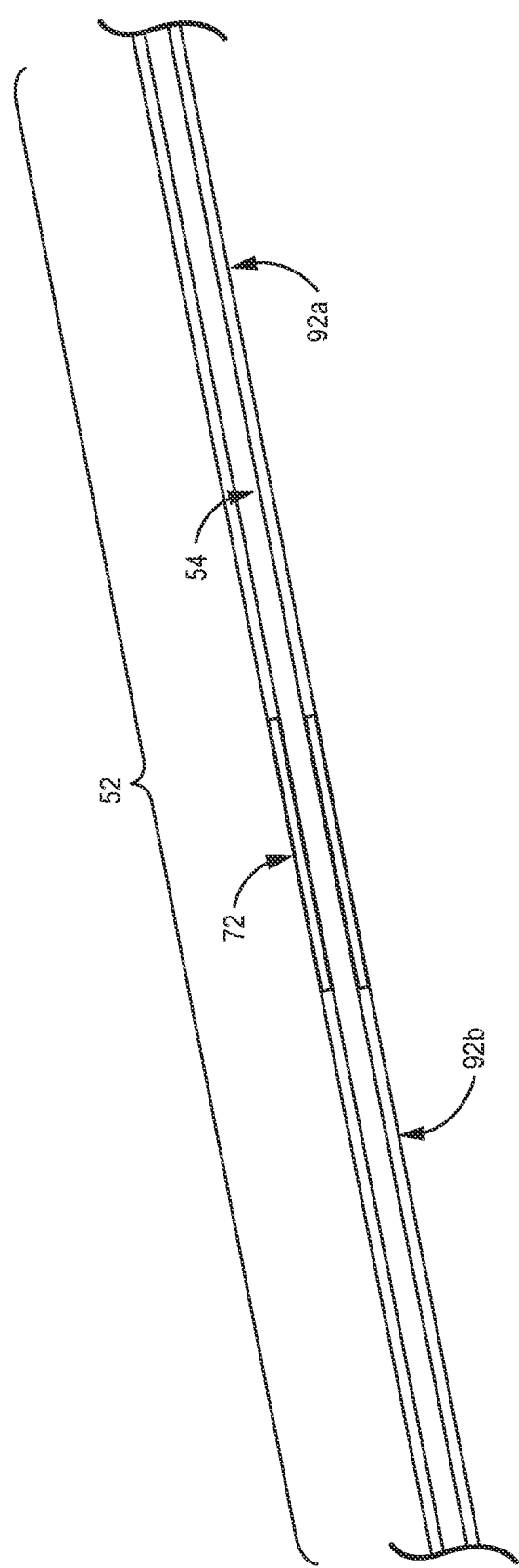
FIG. 8 is a cutaway view of a portion of the deflectable extraluminal section, in accordance with an embodiment of the invention.

Referring now to FIG. 8, a cutaway view of a portion of the deflectable extraluminal section is shown, in accordance with an embodiment of the invention. As shown in FIG. 8, in one embodiment, the deflectable extraluminal section 52 of the second wire 54 may include electrode ring 72 and a dielectric or insulative material 92a and 92b. In particular, the electrode ring 72 may be disposed between insulative material 92a and 92b. The insulative material 92a and 92b may be formed over the second wire 54 adjacent to the electrode ring 72 to provide insulation. While an electrode ring 72 is shown in FIG. 8, in another embodiment, radiopaque markers may be used instead of the electrode ring 72 or in addition to the electrode ring 72. Suitable radiopaque markers include materials that are visible under X-ray, such as one or more of platinum, silver, gold, tantalum, other precious metals, and ceramic materials. In another embodiment, optical conduits, such as core fibers or multi-core fibers, that include fiber Bragg gratings may similarly be used alternatively or additionally. In another embodiment, the deflectable extraluminal section 52 of the second wire 54 may include one or more temperature sensors, such as the thermocouples, thermistors, and/or multi-core fibers or fiber cores described above.

Figure 9:
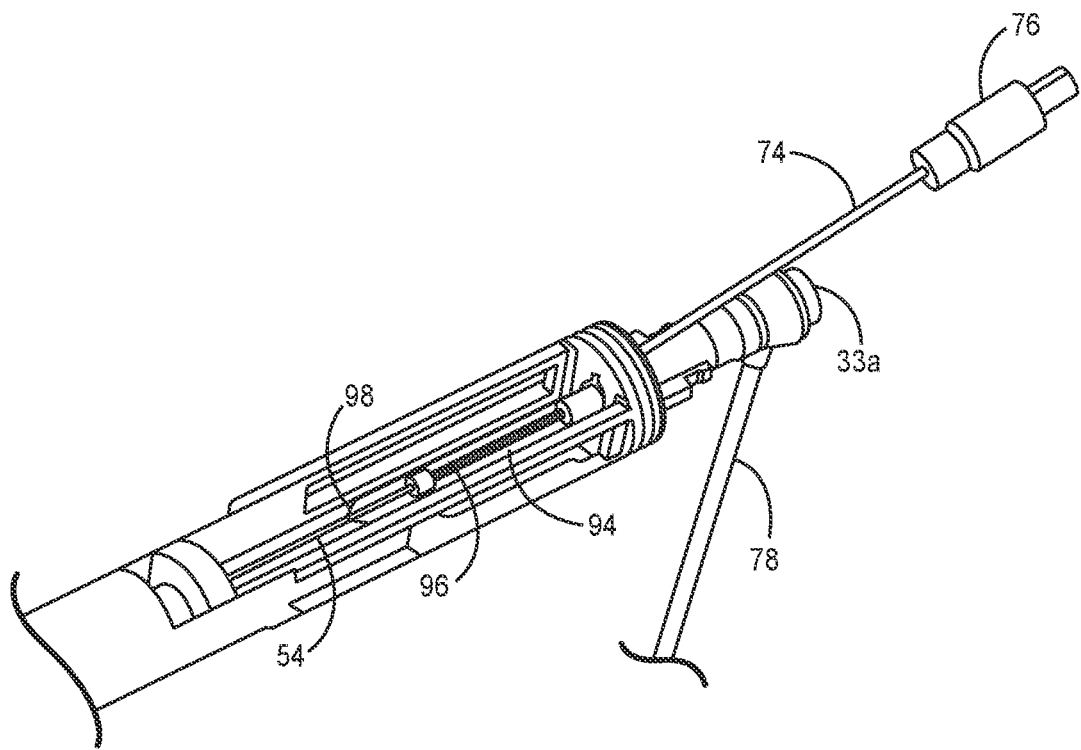
FIG. 9 is an isometric view of a proximal end portion of a handle assembly, in accordance with an embodiment of the invention.
Figure 10:
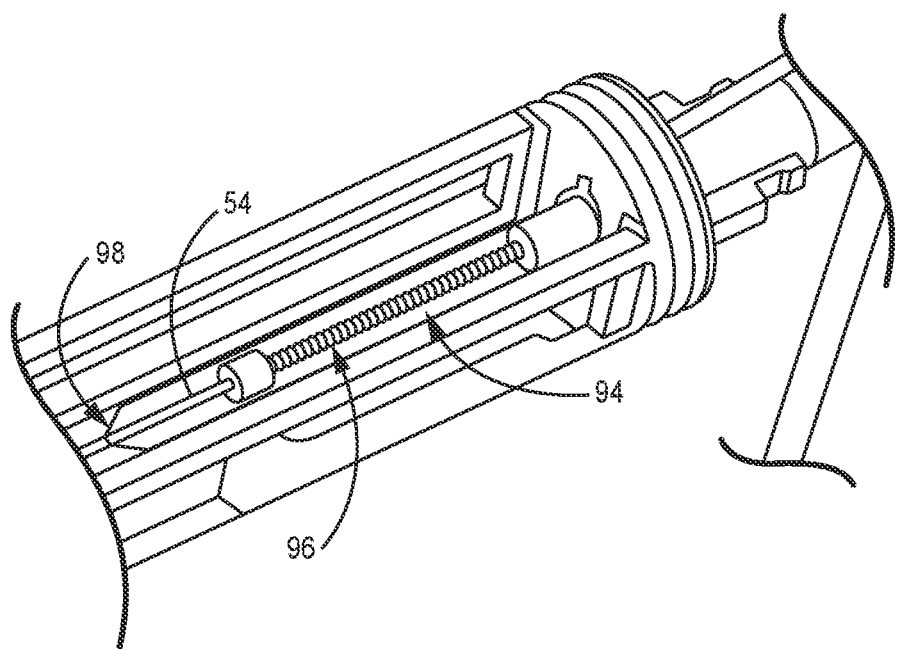
FIG. 10 is another isometric view of a proximal end portion of the handle assembly, in accordance with an embodiment of the invention.

Referring now to FIGS. 9 to 10, an isometric view of a proximal end portion of a handle assembly (FIG. 9) and another isometric view of a proximal end portion of the handle assembly (FIG. 10) are shown, in accordance with embodiments of the invention. The proximal end portion 33a of the handle assembly 30 is shown in order to illustrate fluid lumen 94 and wire tensioner component 96. The fluid lumen 94 may be in fluid communication with tubing 78 and connector 80 (not shown) to deliver fluid down the elongate shaft 40 (not shown). The fluid lumen may have a tapering portion 98 to facilitate fluid transport through the handle assembly 30. In one embodiment, fluid may be delivered down the elongate shaft 40 via fluid lumen 94 to modulate the temperature of tissue proximal to or in contact with the elongate shaft 40 through irrigation of the tissue. The wire tensioner component 96 may be attached to the second wire 54, thereby permitting the second wire 54 and deflectable extraluminal section 52 to deflect independently of deflectable section 42. The wire tensioner component 96 may include a material exhibiting elastic qualities. For example, in some embodiments, the wire tensioner component 96 is a spring (e.g., a helical spring), an elastic band, or another similar material or component.

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it may be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

Although at least one embodiment for an esophageal deviator has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and may include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure may be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A medical device for displacing an esophagus of a subject during a medical procedure, the medical device comprising:
   a handle assembly including a wire tensioner component and an adjustment knob;
   an elongate shaft coupled to the handle assembly, an outermost wall of the elongate shaft defining a lumen, the elongate shaft including a deflectable section;
   a first wire coupled to the adjustment knob and extending from the adjustment knob through the lumen to at least a distal end portion of the deflectable section; and
   a second wire coupled to the wire tensioner component and extending from the wire tensioner component to at least the distal end portion of the deflectable section, the second wire having a deflectable extraluminal section where the second wire exits the lumen of the elongate shaft through an opening, the deflectable extraluminal section configured to deflect independently of the deflectable section, wherein the second wire reenters the lumen through a second opening, wherein the opening forms a first seal around the second wire and the second opening forms a second seal around the second wire, wherein the first seal and the second seal are configured to prevent fluid exchange through the opening and the second opening.

2. The medical device of claim 1, wherein the deflectable section of the elongate shaft includes at least one of the following: an electrode, a radiopaque marker band, a temperature sensor, and a multi-core fiber.

3. The medical device of claim 2, wherein the adjustment knob configured to rotate about a longitudinal axis of the handle assembly.

4. The medical device of claim 2, wherein the deflectable section includes at least one rigid section between two compressible joints.

5. The medical device of claim 2, wherein the first and second wires are in physical contact with each other within the lumen at the distal end portion of the deflectable section.

6. The medical device of claim 2, wherein the first and second wires are bonded to each other within the lumen at the distal end portion of the deflectable section.

7. The medical device of claim 2, wherein the wire tensioner component is configured to provide a tension on the second wire in a neutral position, wherein the first wire is non-tensioned in the neutral position.

8. The medical device of claim 2, wherein rotation of the adjustment knob in a first direction causes the deflectable section of the elongate shaft to deflect.

9. The medical device of claim 2, wherein the deflectable extraluminal section of the second wire deflects in response to contact with a trailing edge of the esophagus of the subject.

10. A deflectable member of a medical device for displacing an esophagus of a subject during a medical procedure, the deflectable member comprising:
    an elongate shaft, an outermost wall of the elongate shaft defining a lumen, the elongate shaft including a deflectable section, wherein the deflectable section is configured to shift between a neutral position and a deflected position through activation of a first wire via an adjustment knob; and
    a second wire having a deflectable extraluminal section where the second wire exits the lumen of the elongate shaft through an opening, the deflectable extraluminal section extending between proximal and distal end portions of the deflectable section,
    wherein the wire tensioner component elongates under a tensile load,
    wherein the deflectable extraluminal section is configured to deflect independently of the deflectable section.

11. The deflectable member of claim 10, wherein the deflectable section of the elongate shaft includes at least one the following: an electrode, a radiopaque marker band, and a multi-core fiber.

12. The deflectable member of claim 10, wherein the deflectable extraluminal section of the second wire includes at least one of the following: an electrode, a radiopaque marker band, a temperature sensor and a multi-core fiber.

13. The deflectable member of claim 10, wherein the adjustment knob is independent from the wire tensioner component.

14. The deflectable member of claim 12, wherein the temperature sensor is a thermocouple, a thermistor, or a core of a multi-core fiber.

15. The deflectable member of claim 10, wherein the deflectable section includes at least one rigid section between two compressible joints.

16. The deflectable member of claim 10, wherein the first and second wires are in physical contact with each other within the lumen at the distal end portion of the deflectable section, wherein the first and second wires independently carry a tensile and/or compressive load.

17. The deflectable member of claim 10, wherein the first and second wires are bonded to each other within the lumen at the distal end portion of the deflectable section.

18. The deflectable member of claim 10, wherein the deflectable extraluminal section of the second wire deflects in response to contact with a trailing edge of the esophagus of the subject.

19. A medical device for displacing an esophagus of a subject during a medical procedure, the medical device comprising:
    a handle assembly including a wire tensioner component and an adjustment knob;
    an elongate shaft coupled to the handle assembly, an outermost wall of the elongate shaft defining a lumen, the elongate shaft including a deflectable section;
    a first wire coupled to the adjustment knob and extending from the adjustment knob through the lumen to at least a distal end portion of the deflectable section; and
    a second wire coupled to the wire tensioner component and extending from the wire tensioner component to at least the distal end portion of the deflectable section, the second wire having a deflectable extraluminal section where the second wire exits the lumen of the elongate shaft through an opening, the deflectable extraluminal section configured to deflect independently of the deflectable section, wherein the wire tensioner component elongates under a tensile load, wherein the wire tensioner component includes a spring, and wherein the spring mechanically couples the second wire to the handle assembly.

* * * * *